United States Patent [19]

Jelich et al.

[11] Patent Number: 4,981,507

[45] Date of Patent: Jan. 1, 1991

[54] HERBICIDAL TRIAZOLOAZINES

[75] Inventors: Klaus Jelich, Wuppertal; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 333,480

[22] Filed: Apr. 5, 1989

[30] Foreign Application Priority Data

Apr. 14, 1988 [DE] Fed. Rep. of Germany ....... 3812350

[51] Int. Cl.$^5$ .................... A01N 43/48; C07D 471/02
[52] U.S. Cl. .......................... 71/92; 71/93; 544/212; 544/263; 544/184
[58] Field of Search ........................ 544/184, 263, 212; 71/92

[56] References Cited

U.S. PATENT DOCUMENTS

| | | | |
|---|---|---|---|
| 3,846,423 | 11/1974 | Kobe | 544/212 |
| 3,910,907 | 10/1975 | O'Brien | 514/212 |
| 4,036,840 | 7/1977 | O'Brien et al. | 544/263 |
| 4,528,288 | 7/1985 | Wade | 544/263 |
| 4,605,433 | 8/1986 | Pearson et al. | 544/212 |
| 4,685,958 | 8/1987 | Pearson et al. | 71/93 |
| 4,854,964 | 8/1989 | Jelich et al. | 544/263 |
| 4,904,301 | 2/1990 | Pearson et al. | 71/92 |
| 4,908,293 | 3/1990 | Katoh | 430/264 |

FOREIGN PATENT DOCUMENTS

| | | |
|---|---|---|
| 0142152 | 5/1985 | European Pat. Off. . |
| 0150974 | 8/1985 | European Pat. Off. . |
| 0197895 | 10/1986 | European Pat. Off. . |
| 0244847 | 11/1987 | European Pat. Off. . |
| 0256396 | 2/1988 | European Pat. Off. . |
| 3729724 | 3/1988 | Fed. Rep. of Germany . |
| 2384282 | 10/1978 | France . |
| 130284 | 3/1978 | German Democratic Rep. . |

OTHER PUBLICATIONS

Okabe et al., J. Heterocyclic Chem., 20, pp. 735–751 p8 1983].
Chem. Abstr. vol. 109 Endy 83206 (1988) Abstracting OLS 3729724.
Chem. Abstr. vol. 87 Entry 17148Y (Maekawa) (1977).
Chem. Abstr. vol. 83 Entry 127285v (1977) (Okabe).
Chem. Abstr. vol. 91, Entry 184908K (1979) Abstracting D. D. 130284.
Chem. Abstr. vol. 91 Endy 66266b (1979) Abstracting French 2,384,282.

*Primary Examiner*—Donald G. Daus
*Attorney, Agent, or Firm*—Sprung Horn Kramer & Woods

[57] ABSTRACT

Herbicidal triazoloazines of the formula

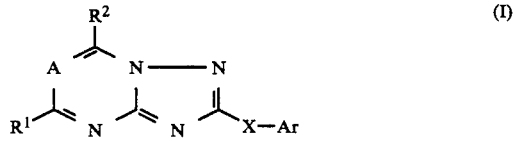

in which

A stands for nitrogen or for a radical C—R$^3$,

R$^1$, R$^2$ and R$^3$ independently of one another each stand for hydrogen, hydroxyl, halogen, for optionally substituted alkyl, for alkoxy, alkylthio or for optionally substituted aryl, or either R$^1$ *and* R$^3$ together or R$^3$ and R$^2$ together stand for a fused, optionally substituted carbocyclic or heterocyclic ring, X stands for oxygen, sulphur, a sulphinyl group, or a sulphonyl group and Ar stands for in each case optionally substituted aryl or heteroaryl.

7 Claims, No Drawings

HERBICIDAL TRIAZOLOAZINES

The invention relates to new triazoloazines, several processes for their preparation and their use as herbicides.

It has been disclosed that certain triazolopyrimidines, such as, for example, the compound 5,7-dimethyl-N-(2-methoxycarbonylphenyl)-1,2,4-triazolo[1,5-a]pyrimidine-2-sulphonamide, possess herbicidal properties (cf., for example, EP No. 142,152 corresponding to U.S. Pat. No. 4,755,212).

However, the herbicidal activity of these previously known compounds against problem weeds and their tolerance by important crop plants are not completely satisfactory in all fields of application.

New triazoloazines of the general formula (I)

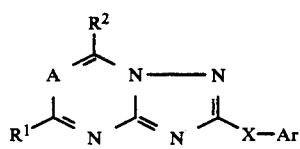

(I)

in which
  A stands for nitrogen or for a radical C—$R^3$, $R^1$, $R^2$ and $R^3$ independently of one another each stand for hydrogen, hydroxyl, halogen, for optionally substituted alkyl, for alkoxy, alkylthio or for optionally substituted aryl or either $R^1$ and $R^3$ together or $R^3$ and $R^2$ together stand for a fused, optionally substituted carbocyclic or heterocyclic ring,
  X stands for oxygen, sulphur, a sulphinyl group or a sulphonyl group and
  Ar stands for in each case optionally substituted aryl or heteroaryl,
have been found.

Furthermore, it has been found that the new triazoloazines of the general formula (I)

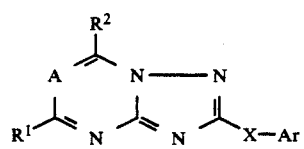

(I)

in which
  A stands for nitrogen or for a radical C—$R^3$, $R^1$, $R^2$ and $R^3$ independently of one another each stand for hydrogen, hydroxyl, halogen, for optionally substituted alkyl, for alkoxy, alkylthio or for optionally substituted aryl or either $R^1$ and $R^3$ together or $R^3$ and $R^2$ together stand for a fused, optionally substituted carbocyclic or heterocyclic ring,
  X stands for oxygen, sulphur, a sulphinyl group or a sulphonyl group and
  Ar stands for in each case optionally substituted aryl or heteroaryl,
are obtained by one of the processes described below:
  (a) triazoloazines of the formula (Ia)

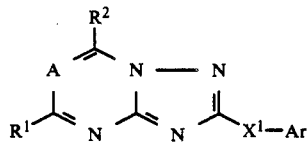

(Ia)

in which
  $X^1$ stands for oxygen or sulphur and
  $R^1$, $R^2$, A and Ar have the abovementioned meaning,
are obtained when triazoloazine derivatives of the formula

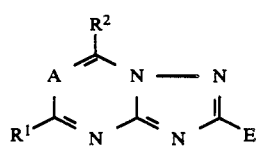

(II)

in which
  E stands for halogen, for alkylthio or for alkylsulphonyl and
  $R^1$, $R_2$ and A have the abovementioned meaning,
are reacted with aromatic alcohols or thiols of the formula (III)
  Ti Ar—$X^1$—H (III)
in which
  $X^1$ and Ar have the abovementioned meaning,
if appropriate in the presence of a diluent and if appropriate in the presence of a reaction auxiliary;
  (b) triazoloazines of the formula (Ib)

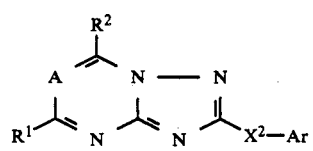

(Ib)

in which
  $X^2$ stands for a sulphinyl group or a sulphonyl group and
  $R^1$, $R^2$, A and Ar have the abovementioned meaning,
are obtained when the triazoloazines, which can be obtained with the aid of process (a), of the formula (Ic)

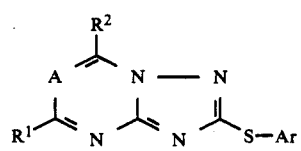

(Ic)

in which
  $R^1$, $R^2$, A and Ar have the abovementioned meaning,
are reacted with an oxidizing agent, if appropriate in the presence of a diluent and if appropriate in the presence of a catalyst.

Finally, it has been found that the new triazoloazines of the general formula (I) possess good herbicidal properties.

Surprisingly, the triazoloazines of the general formula (I) according to the invention show a considerably better herbicidal activity than the triazolopyrimidines which are known from the prior art, such as, for example, the compound 5,7-dimethyl-N-(2-methoxycarbonylphenyl)-1,2,4-triazolo[1,5-a]pyrimidine-2-sulphonamide which are chemically similar compounds of a similar type of action.

Formula (I) provides a general definition of the triazoloazines according to the invention. Preferred compounds of the formula (I) are those in which A stands for nitrogen or for a radical C—R$^3$, R$^1$, R$^2$ and R$^3$ independently of one another each stand for hydrogen, hydroxyl, fluorine, chlorine, bromine, iodine, for in each case straight-chain or branched alkyl, alkoxy or alkylthio, each having 1 to 6 carbon atoms, for in each case straight-chain or branched alkoxyalkyl or alkylthioalkyl, each having 1 to 6 carbon atoms in the individual alkyl moieties, for straight-chain or branched halogenoalkyl having 1 to 4 carbon atoms and 1 to 9 identical or different halogen atoms or for aryl having 6 to 10 carbon atoms which is optionally monosubstituted or polysubstituted by identical or different substituents, suitable substituents being: halogen, cyano, nitro, in each case straight-chain or branched alkyl, alkoxy or alkylthio, each having 1 to 4 carbon atoms, in each case straight-chain or branched halogenoalkyl, halogenoalkoxy or halogenoalkylthio, each having 1 to 4 carbon atoms and 1 to 9 identical or different halogen atoms, or in each case straight-chain or branched alkoxycarbonyl or alkoximinoalkyl, each having 1 to 4 carbon atoms in the individual alkyl moieties; or either R$^1$ and R$^3$ together or R$^3$ and R$^2$ together stand for a fused, saturated or unsaturated carbocyclic or heterocyclic ring which is optionally monosubstituted or polysubstituted by identical or different substituents, it being possible, in the case of the heterocyclic ring, for the ring to contain 1 to 3 identical or different hetero atoms, in particular nitrogen, oxygen or sulphur, suitable substituents in each case being the abovementioned aryl substituents, X stands for oxygen, sulphur, a sulphinyl group or a sulphonyl group and Ar stands for aryl which has 6 to 10 carbon atoms and which is optionally monosubstituted or polysubstituted by identical or different substituents or for a 5-to 7-membered heterocyclic ring containing 1 to 3 hetero atoms (in particular nitrogen, oxygen and/or sulphur) which is optionally monosubstituted or polysubstituted by identical or different substituents and/or benzofused, suitable substituents in each case being: fluorine, chlorine, bromine, iodine, cyano, nitro, hydroxyl, in each case straight-chain or branched alkyl, alkoxy, alkylthio, alkylcarbonyl, alkylsulphinyl or alkylsulphonyl, each having 1 to 6 carbon atoms, in each case straight-chain or branched halogenoalkyl, halogenoalkoxy, halogenoalkylthio, halogenoalkylsulphinyl, halogenoalkylsulphonyl or halogenoalkylcarbonyl, each having 1 to 6 carbon atoms and 1 to 9 identical or different halogen atoms, phenyl, phenoxy, phenylthio, phenylcarbonyl, hydroxycarbonyl, in each case straight-chain or branched alkoxycarbonyl, alkenyloxycarbonyl or alkoxyalkoxycarbonyl, each having 1 to 6 carbon atoms in the individual alkyl moieties or 3 to 6 carbon atoms in the alkenyl moiety, and also hydroxyiminoalkyl or straight-chain or branched alkoximinoalkyl, each having 1 to 4 carbon atoms in the individual alkyl moieties.

Particularly preferred compounds of the general formula (I) are those in which

A stands for nitrogen or for a radical C—R$^3$, R$^1$, R$^2$ and R$^3$ independently of one another each stand for hydrogen, hydroxyl, fluorine, chlorine, bromine, for methyl, ethyl, n- or i-propyl, n-, i-, s- or t-butyl, for chloromethyl, dichloromethyl, trichloromethyl, fluoromethyl, difluoromethyl, trifluoromethyl, dichlorofluoromethyl, chlorodifluoromethyl or fluorochloromethyl, for methoxymethyl, ethoxymethyl, n- or i-propoxymethyl, methylthiomethyl, ethylthiomethyl, n- or i-propylthiomethyl, for methoxy, ethoxy, n- or i-propoxy, for methylthio, ethylthio, n- or ipropylthio or for phenyl, X stands for oxygen, sulphur, a sulphinyl group or a sulphonyl group and Ar stands for phenyl or naphthyl, in each case optionally monosubstituted to trisubstituted by identical or different substituents, or for a heterocyclic ring of the formula

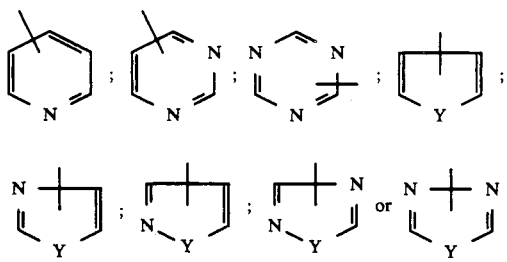

where

Y in each case stands for oxygen, sulphur, an NH group or an N—CH$_3$ group, which heterocyclic ring is optionally monosubstituted to trisubstituted by identical or different substituents and/ or benzofused, suitable phenyl-, naphthyl- and heterocyclyl-substituents in each case being: fluorine, chlorine, bromine, iodine, cyano, nitro, hydroxyl, methyl, ethyl, n- or i-propyl, n-, i-, s- or t-butyl, methoxy, ethoxy, n- or i-propoxy, methylthio, ethylthio, acetyl, propionyl, methylsulphinyl, methylsulphonyl, trifluoromethyl, trifluoromethoxy, trifluoromethylthio, trifluoromethylsulphinyl, trifluoromethylsulphonyl, chloroacetyl, dichloroacetyl, trifluoroacetyl, phenyl, phenoxy, phenylthio, benzoyl, hydroxycarbonyl, methoxycarbonyl, ethoxycarbonyl, n- or i-propoxycarbonyl, allyloxycarbonyl, methoxymethoxycarbonyl, ethoxyethoxycarbonyl, hydroxyiminomethyl, methoxyiminomethyl, methoximinoethyl and ethoximinoethyl.

Very particularly preferred compounds of the general formula (I) are those in which A stands for nitrogen or for a CH group, R$^1$ and R$^2$ independently of one another stand for hydrogen, for methyl, ethyl, n- or i-propyl, n-, i-, s- or t-butyl, for methoxymethyl, ethoxymethyl, n- or i-propoxymethyl, for methylthiomethyl, for trifluoromethyl, trichloromethyl, for dichlorofluoromethyl, chlorodifluoromethyl, for methoxy, ethoxy, n- or i-propoxy, methylthio or ethylthio, X stands for oxygen, sulphur, a sulphinyl group or a sulphonyl group and Ar stands for phenyl, α-naphthyl or β-naphthyl, in each case optionally monosubstituted to trisubstituted by identical or different substituents, or for a heterocyclic ring of the formula

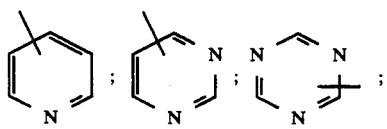

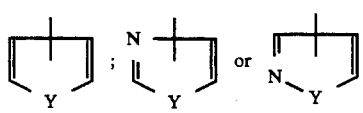

where Y in each case stands for oxygen, sulphur, an NH group or an N—CH₃ group, which heterocyclic ring is optionally monosubstituted to trisubstituted by identical or different substituents and/or benzo-fused, suitable phenyl-, naphthyl- and heterocyclyl-substituents in each case being: fluorine, chlorine, bromine, iodine, cyano, nitro, hydroxyl, methyl, ethyl, methoxy, methylthio, acetyl, trifluoromethyl, trifluoromethoxy, trifluoromethylthio, phenyl, phenoxy, phenylthio, hydroxycarbonyl, methoxycarbonyl, ethoxycarbonyl, allyloxycarbonyl, ethoxyethoxycarbonyl, hydroximinomethyl, methoximinomethyl or methoximinoethyl.

Especially preferred compounds of the formula (I) are those in which

A stands for a CH group,

R¹ stands for methyl, methoxy, methoxymethyl or trifluoromethyl,

R² stands for hydrogen, methyl, methoxy, methoxymethyl or trifluoromethyl,

X stands for oxygen, sulphur or a sulphonyl group and

Ar stands for phenyl, pyridyl or pyrimidyl, in each case optionally monosubstituted to trisubstituted by identical or different substituents, suitable substituents in each case being: fluorine, chlorine, bromine, cyano, nitro, hydroxyl, methyl, ethyl, t-butyl, methoxy, methylthio, acetyl, trifluoromethyl, trifluoromethoxy, trifluoromethylthio, phenyl, phenoxy, phenylthio, hydroxycarbonyl, methoxycarbonyl, ethoxycarbonyl, allyloxycarbonyl, ethoxyethoxycarbonyl, hydroximinomethyl, methoximinomethyl or methoximinoethyl.

In addition to the compounds mentioned in the Preparation Examples, the following triazoloazines of the general formula (I)

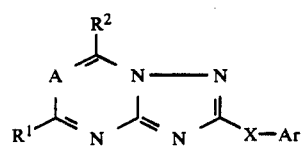

may be mentioned individually:

TABLE 1

| R¹ | R² | A | X | Ar |
|---|---|---|---|---|
| CH₃ | CH₃ | CH | O | ![benzene with CH₃ and C₂H₅] |
| CH₃ | CH₃ | CH | O | ![benzene with CH₃ and OCH₃] |
| CH₃ | CH₃ | CH | O | ![benzene with CH₃, CH₃, CH₃] |
| CH₃ | CH₃ | CH | O | ![benzene with CH₃ and Cl] |
| CH₃ | CH₃ | CH | O | ![benzene with CH₃ and Br] |
| CH₃ | CH₃ | CH | O | ![benzene with C₂H₅] |
| CH₃ | CH₃ | CH | O | ![benzene with Cl, Cl, Cl] |
| CH₃ | CH₃ | CH | O | ![benzene with Br and C₂H₅] |
| CH₃ | CH₃ | CH | O | ![benzene with COOCH₃] |
| CH₃ | CH₃ | CH | O | ![benzene with COOCH₃ and CH₃] |

TABLE 1-continued

| R¹ | R² | A | X | Ar |
|----|----|----|----|----|
| CH₃ | CH₃ | CH | O | 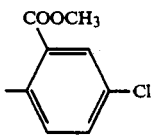 |
| CH₃ | CH₃ | CH | S | 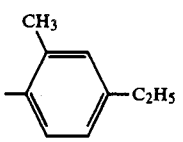 |
| CH₃ | CH₃ | CH | S | 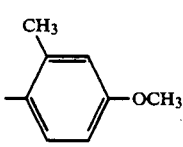 |
| CH₃ | CH₃ | CH | S | 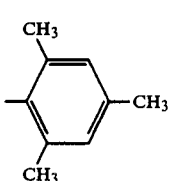 |
| CH₃ | CH₃ | CH | S | 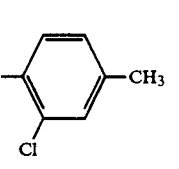 |
| CH₃ | CH₃ | CH | S | 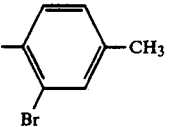 |
| CH₃ | CH₃ | CH | S | 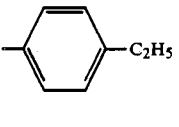 |
| CH₃ | CH₃ | CH | S | 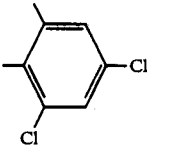 |
| CH₃ | CH₃ | CH | S | 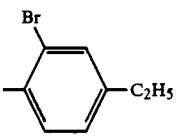 |
| CH₃ | CH₃ | CH | S | 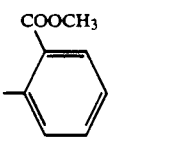 |
| CH₃ | CH₃ | CH | S |  |
| CH₃ | CH₃ | CH | S |  |
| CH₃ | CH₃ | CH | $-\overset{\overset{O}{\|}}{S}-$ | 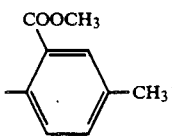 |
| CH₃ | CH₃ | CH | $-\overset{\overset{O}{\|}}{S}-$ | 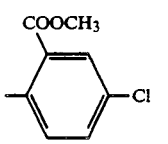 |
| CH₃ | CH₃ | CH | $-\overset{\overset{O}{\|}}{S}-$ | 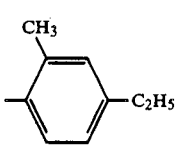 |
| CH₃ | CH₃ | CH | $-\overset{\overset{O}{\|}}{S}-$ | 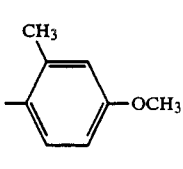 |
| CH₃ | CH₃ | CH | $-\overset{\overset{O}{\|}}{S}-$ | 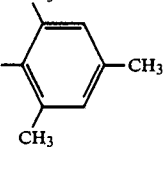 |
| CH₃ | CH₃ | CH | $-\overset{\overset{O}{\|}}{S}-$ | 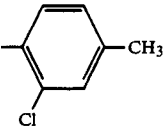 |
| CH₃ | CH₃ | CH | $-\overset{\overset{O}{\|}}{S}-$ | 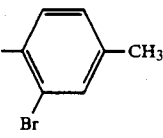 |
| CH₃ | CH₃ | CH | $-\overset{\overset{O}{\|}}{S}-$ | 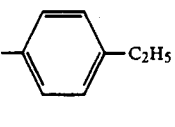 |

TABLE 1-continued

| R¹ | R² | A | X | Ar |
|---|---|---|---|---|
| CH₃ | CH₃ | CH | –S(O)– | 2-COOCH₃, 6-CH₃-phenyl |
| CH₃ | CH₃ | CH | –S(O)– | 2-COOCH₃, 5-CH₃-phenyl |
| CH₃ | CH₃ | CH | –S(O)– | 2-COOCH₃, 5-Cl-phenyl |
| CH₃ | CH₃ | CH | –SO₂– | 2-CH₃, 4-C₂H₅-phenyl |
| CH₃ | CH₃ | CH | –SO₂– | 2-CH₃, 4-OCH₃-phenyl |
| CH₃ | CH₃ | CH | –SO₂– | 2,4,6-tri-CH₃-phenyl |
| CH₃ | CH₃ | CH | –SO₂– | 2-Cl, 4-CH₃-phenyl |
| CH₃ | CH₃ | CH | –SO₂– | 2-Br, 4-CH₃-phenyl |
| CH₃ | CH₃ | CH | –SO₂– | 4-C₂H₅-phenyl |
| CH₃ | CH₃ | CH | –SO₂– | 2,4,6-tri-Cl-phenyl |
| CH₃ | CH₃ | CH | –SO₂– | 2-Cl, 4-C₂H₅-phenyl |
| CH₃ | CH₃ | CH | –SO₂– | 2-COOCH₃-phenyl |
| CH₃ | CH₃ | CH | –SO₂– | 2-COOCH₃, 5-CH₃-phenyl |
| CH₃ | CH₃ | CH | –SO₂– | 2-COOCH₃, 4-OCH₃-phenyl |
| CH₃ | CH₃ | N | O | 2-CH₃-phenyl |
| CH₃ | CH₃ | N | O | 2-CH₃, 4-Cl-phenyl |
| CH₃ | CH₃ | N | O | 4-C(CH₃)₃-phenyl |
| CH₃ | CH₃ | N | O | 2,4-di-CH₃-phenyl |
| CH₃ | CH₃ | N | O | 2-COOCH₃-phenyl |
| CH₃ | CH₃ | N | S | 2-CH₃-phenyl |
| CH₃ | CH₃ | N | S | 2-CH₃, 4-Cl-phenyl |

TABLE 1-continued

| R¹ | R² | A | X | Ar |
|---|---|---|---|---|
| CH₃ | CH₃ | N | S | 2,5-dimethylphenyl |
| CH₃ | CH₃ | N | S | 4-tert-butylphenyl |
| CH₃ | CH₃ | N | S | 2-(COOCH₃)phenyl |
| CH₃ | CH₃ | N | —SO₂— | 2-methylphenyl |
| CH₃ | CH₃ | N | —SO₂— | 2,5-dimethylphenyl |
| CH₃ | CH₃ | N | —SO₂— | 2-methyl-4-chlorophenyl |
| CH₃ | CH₃ | N | —SO₂— | 4-tert-butylphenyl |
| CH₃ | CH₃ | N | —SO₂— | 2-(COOCH₃)-5-methylphenyl |
| CH₃ | CH₃ | N | —SO₂— | 2-methyl-4-methoxyphenyl |
| CH₃ | CH₃ | N | —S(O)— | 2-methylphenyl |
| CH₃ | CH₃ | N | —S(O)— | 2,5-dimethylphenyl |
| CH₃ | CH₃ | N | —S(O)— | 2-methyl-4-chlorophenyl |
| CH₃ | CH₃ | N | —S(O)— | 4-tert-butylphenyl |
| CH₃ | CH₃ | N | —S(O)— | 2-(COOCH₃)phenyl |
| CH₃ | OCH₃ | CH | O | 2-methylphenyl |
| CH₃ | OCH₃ | CH | O | 2,5-dimethylphenyl |
| CH₃ | OCH₃ | CH | O | 2-methyl-4-chlorophenyl |
| CH₃ | OCH₃ | CH | O | 4-tert-butylphenyl |
| CH₃ | OCH₃ | CH | O | 2-(COOCH₃)phenyl |
| CH₃ | OCH₃ | CH | O | 2-methyl-4-methoxyphenyl |
| CH₃ | OCH₃ | CH | S | 2-methylphenyl |
| CH₃ | OCH₃ | CH | S | 2,5-dimethylphenyl |

TABLE 1-continued
| R¹ | R² | A | X | Ar |
|---|---|---|---|---|
| CH₃ | OCH₃ | CH | S | 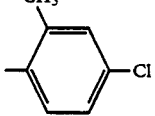 |
| CH₃ | OCH₃ | CH | S | 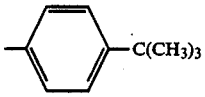 |
| CH₃ | OCH₃ | CH | S | 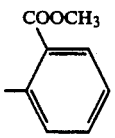 |
| CH₃ | OCH₃ | CH | S | 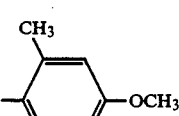 |
| CH₃ | OCH₃ | CH | −S(=O)− |  |
| CH₃ | OCH₃ | CH | −S(=O)− | 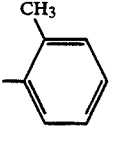 |
| CH₃ | OCH₃ | CH | −S(=O)− | 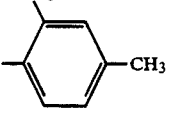 |
| CH₃ | OCH₃ | CH | −S(=O)− | 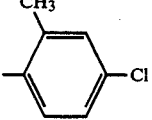 |
| CH₃ | OCH₃ | CH | −S(=O)− | 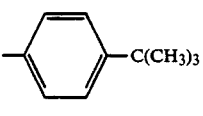 |
| CH₃ | OCH₃ | CH | −SO₂− | 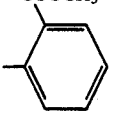 |
| CH₃ | OCH₃ | CH | −SO− | 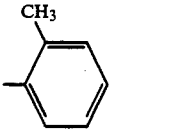 |
| CH₃ | OCH₃ | CH | −SO₂− | 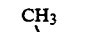 |
| CH₃ | OCH₃ | CH | −SO₂− | 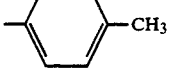 |
| CH₃ | OCH₃ | CH | −SO₂− | 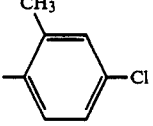 |
| CH₃ | OCH₃ | CH | −SO₂− | 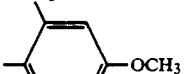 |
| OCH₃ | OCH₃ | CH | O |  |
| OCH₃ | OCH₃ | CH | O | 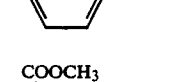 |
| OCH₃ | OCH₃ | CH | O | 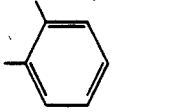 |
| OCH₃ | OCH₃ | CH | O | 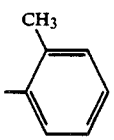 |
| OCH₃ | OCH₃ | CH | O | 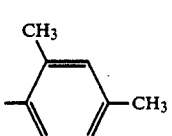 |
| OCH₃ | OCH₃ | CH | S | 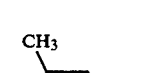 |
| OCH₃ | OCH₃ | CH | S | 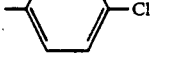 |

TABLE 1-continued
| R¹ | R² | A | X | Ar |
|---|---|---|---|---|
| OCH₃ | OCH₃ | CH | S | 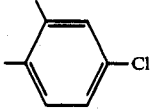 |
| OCH₃ | OCH₃ | CH | S | 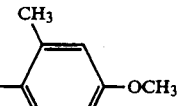 |
| OCH₃ | OCH₃ | CH | S | 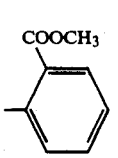 |
| OCH₃ | OCH₃ | CH | S | 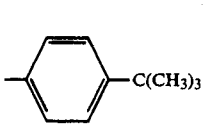 |
| OCH₃ | OCH₃ | CH | —S(O)— | 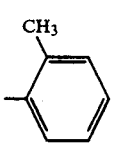 |
| OCH₃ | OCH₃ | CH | —S(O)— | 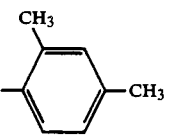 |
| OCH₃ | OCH₃ | CH | —S(O)— | 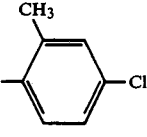 |
| OCH₃ | OCH₃ | CH | —S(O)— | 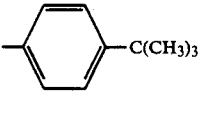 |
| OCH₃ | OCH₃ | CH | —S(O)— | 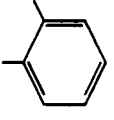 |
| OCH₃ | OCH₃ | CH | —SO₂— | 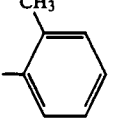 |
| OCH₃ | OCH₃ | CH | —SO₂— | 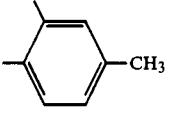 |
TABLE 1-continued
| R¹ | R² | A | X | Ar |
|---|---|---|---|---|
| OCH₃ | OCH₃ | CH | —SO₂— | 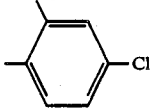 |
| OCH₃ | OCH₃ | CH | —SO₂— | 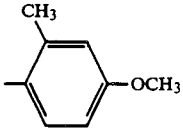 |
| OCH₃ | OCH₃ | CH | —SO₂— | 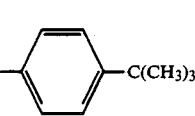 |
| OCH₃ | OCH₃ | CH | —SO₂— | 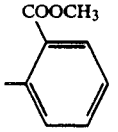 |
| CH₃ | CH₃ | CH | O |  |
| CH₃ | CH₃ | CH | O | 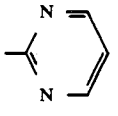 |
| CH₃ | CH₃ | CH | O | 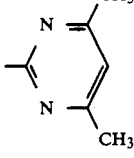 |
| CH₃ | CH₃ | CH | O | 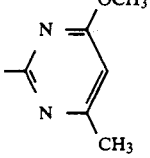 |
| CH₃ | CH₃ | CH | O |  |
| CH₃ | CH₃ | CH | —S— | |
| CH₃ | CH₃ | CH | —S— | 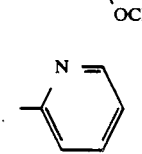 |

TABLE 1-continued

| R¹ | R² | A | X | Ar |
|---|---|---|---|---|
| CH₃ | CH₃ | CH | —S— | (4,6-dimethylpyrimidin-2-yl) |
| CH₃ | CH₃ | CH | —S— | (4,6-dimethoxypyrimidin-2-yl) |
| CH₃ | CH₃ | CH | —S(O)— | (pyridin-2-yl) |
| CH₃ | CH₃ | CH | —S(O)— | (pyrimidin-2-yl) |
| CH₃ | CH₃ | CH | —S(O)— | (4,6-dimethylpyrimidin-2-yl) |
| CH₃ | CH₃ | CH | —SO₂— | (pyridin-2-yl) |
| CH₃ | CH₃ | CH | —SO₂— | (pyrimidin-2-yl) |
| CH₃ | CH₃ | CH | —SO₂— | (4,6-dimethylpyrimidin-2-yl) |
| CH₃ | CH₃ | CH | —SO₂— | (4,6-dimethoxypyrimidin-2-yl) |

If, for example, 2-chloro-5,7-dimethyl-1,2,4triazolo[1,5-a]pyrimidine and 2-chlorothiophenol are used as starting substances, the course of the reaction of process (a) according to the invention may be represented by the following equation:

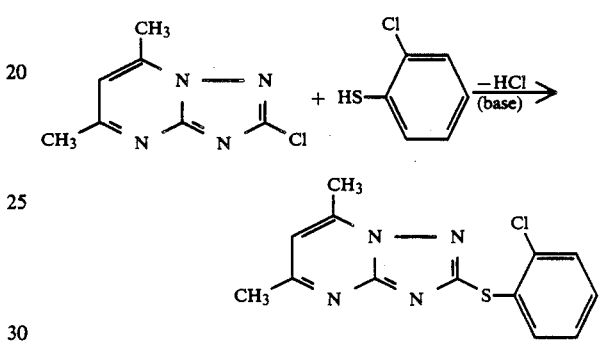

If, for example, 2-(2-chlorophenylthio)-5,7-dimethyl-1,2,4-triazolo[1,5-a]pyrimidine is used as starting compound and 3-chloroperbenzoic acid is used as oxidizing agent, the course of the reaction of process (b) according to the invention may be represented by the following equation:

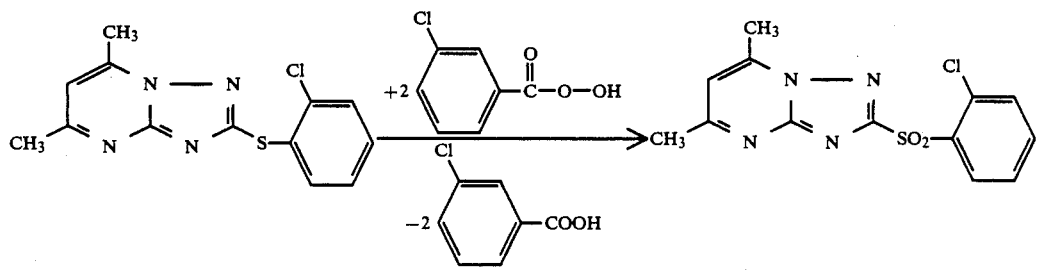

Formula (II) provides a general definition of the triazoloazine derivatives required as starting substances for carrying out process (a) according to the invention. In this formula (II), $R^1$, $R^2$ and A preferably stand for those radicals which have already been mentioned in connection with the description of the substances of the formula (I) according to the invention as being preferred for these substituents.

E in formula (II) preferably stands for chlorine, bromine or iodine, in particular for chlorine or bromine, or for in each case straight-chain or branched alkylthio or alkylsulphonyl, in each case having 1 to 4 carbon atoms.

The triazoloazine derivatives of the formula (II) are known or can be obtained in analogy to known processes (cf., for example, J. Heterocycl. Chem. 20, 735 751 [1983]; J. chem. Soc. C 1966, 2031–2038; Jp. 55/113,043; J. Prakt. Chem. 314; 515–524 [1972]; DE 2,327,133; U.S. Pat. No. 4,036,840; J. chem. Soc. Perkin Trans. I 1979, 3085—3094; Austral. J. Chem. 32, 2727-2732 [1979]Sci. 28, 121-127 [1980]; Synthesis 1983, 44–47; EP No. 197,895).

Formula (III) provides a general definition of the aromatic alcohols or thiols also required as starting substances for carrying out process (a) according to the invention. In this formula (III), Ar preferably stands for those radicals which have already been mentioned in connection with the description of the substances of the formula (I) according to the invention as being preferred for this substituent.

$X^1$ in formula (III) preferably stands for oxygen or sulphur.

The aromatic alcohols or thiols of the formula (III) are generally known compounds of organic chemistry.

Formula (Ic) provides a general definition of the triazoloazines required as starting substances for carrying out process (b) according to the invention. In this formula (Ic), $R^1$, $R^2$, A and Ar preferably stand for those radicals which have already been mentioned in connection with the description of the substances of the formula (I) according to the invention as being preferred for these substituents.

The triazoloazines of the formula (Ic) are compounds according to the invention and can be obtained with the aid of process (a) according to the invention.

Suitable diluents for carrying out process (a) according to the invention are inert organic solvents. These include in particular aliphatic, alicyclic or aromatic hydrocarbons, such as, for example, benzine, benzene, toluene, xylene, petroleum ether, hexane and cyclohexane, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide, or sulphones, such as sulpholane.

Process (a) according to the invention is preferably carried out in the presence of a suitable reaction auxiliary. Suitable reaction auxiliaries are all inorganic and organic bases which can customarily be used. Alkali metal hydrides, alkali metal hydroxides, alkali metal amides, alkali metal alkoxides, alkali metal carbonates or alkali metal hydrogen carbonates, such as, for example, sodium hydride, sodium amide, sodium hydroxide, sodium methoxide, sodium ethoxide, potassium t-butoxide, sodium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

When carrying out process (a) according to the invention, the reaction temperatures can be varied within a relatively wide range. In general, the process is carried out at temperatures between 20° C. and 250° C., preferably at temperatures between 80° C. and 230° C.

For carrying out process (a) according to the invention, 0.8 to 2.5 moles, preferably 1.0 to 1.5 moles, of aromatic alcohol or thiol of the formula (III) and if appropriate 0.8 to 2.5 moles, preferably 1.0 to 1.5 moles, of reaction auxiliary are generally employed per mole of triazoloazine derivative of the formula (II).

The reaction is carried out, and the reaction products are worked up and isolated by generally customary methods (cf. also the Preparation Examples).

Oxidizing agents which can be used for carrying out process (b) according to the invention are all inorganic or organic oxidizing agents which are customarily suitable for sulphur oxidations. Organic peracids, such as, for example, peracetic acid, 4-nitroperbenzoic acid or 3-chloroperbenzoic acid, inorganic peracids, such as, for example, periodic acid, and also hydrogen peroxide, potassium permanganate or chromic acid are preferably used.

Suitable diluents for carrying out process (b) according to the invention are also inert organic solvents. Hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide, are preferably used.

If appropriate, process (b) according to the invention can be carried out in the presence of a reaction auxiliary, in particular of an acid-binding agent. Suitable acid-binding agents are all organic and inorganic acid-binding agents which can customarily be used. The hydroxides, acetates or carbonates of alkaline earth metals or alkali metals, such as, for example, calcium hydroxide, sodium hydroxide, sodium acetate or sodium carbonate, are preferably used.

If appropriate, process (b) according to the invention can be carried out in the presence of a suitable catalyst. Suitable catalysts are all catalysts which are customarily customary for sulphur oxidations of this type. Examples which may be mentioned in this connection are heavy-metal catalysts, such as ammonium molybdate.

When carrying out process (b) according to the invention, the reaction temperatures can be varied within a relatively wide range. In general, the process is carried out at temperatures between −20° C. and +150° C., preferably at temperatures between 0° C. and +120° C.

For carrying out process (b) according to the invention, 0.8 to 1.2 moles, preferably equimolar amounts of oxidizing agent are generally employed per mole of triazoloazine of the formula (Ic) if the oxidation of the sulphur is to be interrupted at the sulphoxide stage. In order to carry out oxidation to give the sulphone, 1.8 to 3.0 moles, preferably twice the molar amounts, of oxidizing agent are generally employed per mole of triazoloazine of the formula (Ic). The reaction is carried out and the end products of the formula (Ib) are worked up and isolated by customary methods (cf. also the Preparation Examples).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera. Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Here, the active compounds according to the invention can be employed with particularly good success for combating dicotyledon weeds in monocotyledon crops, such as, for example, barley or wheat.

When applied in suitable application rates, the active compounds according to the invention also show a fungicidal activity and can be employed for example for combating rice diseases, such as, for example against the causative organism of rice blast disease (Pyricularia oryzae).

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable, for example, lignin-sulphite waste liquors and methylcellulose.

Adhesives such as carboxymethylcellulose and natural and synthetic polymers in the form of powders, granules or lattices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1:3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (META-MITRON) for combating weeds in sugar beets, and 4-amino6-(1,1-dimethylethyl)-3-methylthio-1,2,4-triazin-5(4H)one (METRIBUZIN) for combating weeds in soy beans. Mixtures with 2,4-dichlorophenoxyacetic acid (2,4-D); 4-(2,4-dichlorophenoxy)-butyric acid (2,4-DB); 2,4-dichlorophenoxy-propionic acid (2,4-DP); 3-isopropyl-2,1,3-benzo-thiadiazin-4-one 2,2-dioxide (BENTAZONE); methyl 5-(2,4-dichlorophenoxy)-2-nitrobenzoate (BIFENOX); 3,5-dibromo-4-hydroxybenzonitrile (BROMOXYNIL); 2-chloro-N-{[(4-methoxy-6-methyl-1,3,5-triazin-2-yl)-amino]-carbonyl}-benzenesulphonamide (CHLORSULFURON); 2-[4-(2,4-dichlorophenoxy)-phenoxy]-propionic acid, its methyl ester or its ethyl ester (DICLOFOP); 4-amino-6-t-butyl-3-ethylthio-1,2,4-triazin-5(4H)-one (ETHIOZIN); 2-{4-[(6-chloro-2-benzoxazolyl)-oxy]-phenoxy}propanoic acid, its methyl ester or its ethyl ester (FENOXAPROP); [(4-amino-3,5-dichloro-6-fluoro-2-pyridinyl)- oxy]-acetic acid or its 1-4-methyl-heptyl ester (FLU-ROXYPYR); methyl 2-[4,5-dihydro4-methyl-4-(1-methylethyl)-5-oxo-1H-imidazol-2-yl]-4(5)methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)acetic acid (MCPA); (4-chloro-2-methylphenoxy)-propionic acid (MCPP); N-methyl-2-(1,3-benzothiazol-2-yl-oxy)-acetanilide (MEFENACET); 2-{[[((4-methoxy-6-methyl-1,3,5-triazin-2-yl)-amino)-carbonyl]-amino]-sulphonyl}-benzo acid or its methyl ester (METSULFURON); 0-(6-chloro-3-phenyl-pyridazin-4-yl)-S-octyl-thiocarbonate (PYRIDATE); 4-ethylamino-2-t-butylamino-6-methylthio-s-triazine (TERBUTRYNE) and methyl 3-[[[[(4-methoxy-6-methyl-1,3,5-triazin-2-yl)-amino]-carbonyl]-amino]-sulphony]-thiophene-2-carboxylate (THIAMETURON) are also, if appropriate, advantageous. Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied both before and after emergence of the plants.

They can also be incorporated into the soil before sowing.

The amount of active compound used can vary within a relatively wide range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

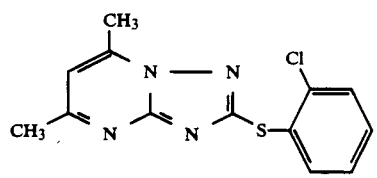

(Process a)

3.8 g (0.034 mole) of potassium t-butoxide and 6.2 g (0.034 mole) of 2-chloro-5,7-dimethyl-1,2,4-triazolo[1,5-a]pyrimidine (cf. J. Chem. Soc. C 1966, 2031–2038) are added in succession to 4.85 g (0.0335 mole) of 2-chlorothiophenol in 20 ml of sulpholane, and the mixture is boiled to reflux for 2 minutes. For working up, the reaction mixture is allowed to cool and poured into ice water, and the precipitated solid is filtered off with suction and recrystallized from aqueous ethanol.

6.5 g (66.7% of theory) of 2-(2-chlorophenyl-thio)-5,7-dimethyl-1,2,4-triazolo[1,5-a]pyrimidine of melting point 143° C. are obtained.

EXAMPLE 2

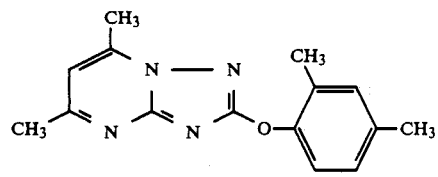

(Process a)

1.35 g (0.0121 mole) of potassium t-butoxide and 2.2 g (0.0121 mole) of 2-chloro-5,7-dimethyl-1,2,4-triazolo[1,5-a]pyrimidine are added in succession to 1.5 g (0.0123 mole) of 2,4-dimethylphenol in 15 ml of sulpholane, and the mixture is heated at boiling point for 15 minutes. For working up, the reaction mixture is allowed to cool and poured into ice water, the mixture is extracted with ethyl acetate, washed with water and dried over sodium sulphate, and the solvent is removed in vacuo.

The residue is purified by chromatography on silica gel (eluent: dichloromethane/acetone 4:1).

1.6 g (49.5% of theory) of 2-(2,4-dimethylphenoxy)-5,7-dimethyl-1,2,4-triazolo[1,5-a]-pyrimidine of melting point 133–136° C. are obtained.

Example 3

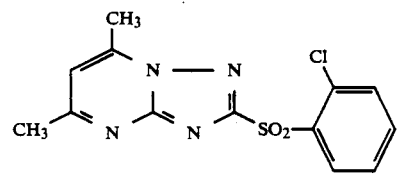

(Process b)

6.5 g (0.038 mole) of 3-chloroperbenzoic acid are added to 3.0 g (0.01 mole) of 2-(2-chlorophenylthio)-5,7-dimethyl-1,2,4-triazolo[1,5-a]pyrimidine in 100 mL of ethyl acetate, and the mixture is boiled to reflux for 2 hours. For working up, the reaction mixture is allowed to cool, washed with aqueous sodium carbonate solution and evaporated in vacuo, and the residue is recrystallized from ethanol.

1.8 g (54% of theory) of 2-(2-chlorophenylsulphonyl)-5,7-dimethyl-1,2,4-triazolo[1,5-a]pyrimid of melting point 184° C. are obtained.

The following triazoloazines of the general formula (I)

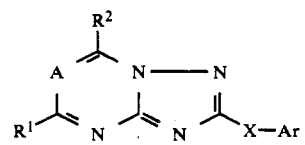

are obtained in a corresponding manner and following the general preparation instructions:

TABLE 2
| Example No. | R¹ | R² | A | X | Ar | Melting point/°C. |
|---|---|---|---|---|---|---|
| 4 | CH₃ | CH₃ | CH | S | 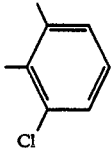 2,6-dichlorophenyl | 165–168 |
| 5 | CH₃ | CH₃ | CH | S | 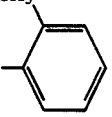 2-methylphenyl | 116–117 |
| 6 | CH₃ | CH₃ | CH | SO₂ | 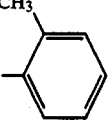 2-methylphenyl | 146–147 |
| 7 | CH₃ | CH₃ | CH | S | 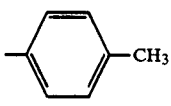 4-methylphenyl | 137–139 |
| 8 | CH₃ | CH₃ | CH | SO₂ | 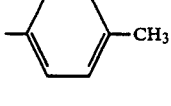 4-methylphenyl | 183–185 |
| 9 | CH₃ | CH₃ | CH | S | 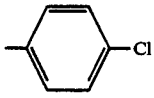 4-chlorophenyl | 169–173 |
| 10 | CH₃ | CH₃ | CH | S | 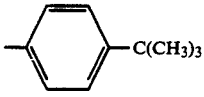 4-tert-butylphenyl | 153–155 |
| 11 | CH₃ | CH₃ | CH | S | 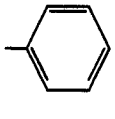 phenyl | 146–148 |
| 12 | CH₃ | CH₃ | CH | SO₂ | 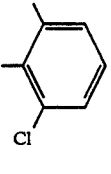 2,6-dichlorophenyl | 126–130 |
| 13 | CH₃ | CH₃ | CH | SO₂ | 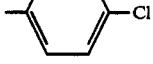 4-chlorophenyl | 172–175 |
| 14 | CH₃ | CH₃ | CH | SO₂ | 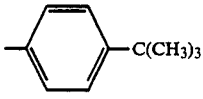 4-tert-butylphenyl | 203–204 |
| 15 | CH₃ | CH₃ | CH | SO₂ | 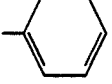 phenyl | 153–155 |

TABLE 2-continued

| Example No. | $R^1$ | $R^2$ | A | X | Ar | Melting point/°C |
|---|---|---|---|---|---|---|
| 16 | $CH_3$ | $CH_3$ | CH | S | 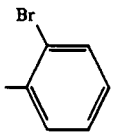 2-Br-phenyl | 143 (Decomposition) |
| 17 | $CH_3$ | $CH_3$ | CH | S | 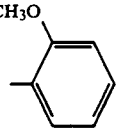 2-$CH_3O$-phenyl | 146 (Decomposition) |
| 18 | $CH_3$ | $CH_3$ | CH | $SO_2$ | 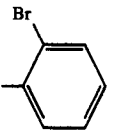 2-Br-phenyl | 180–182 |
| 19 | $CH_3$ | $CH_3$ | CH | $SO_2$ | 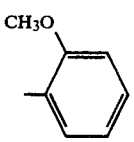 2-$CH_3O$-phenyl | 188–190 |
| 20 | $CH_3$ | $CH_3$ | CH | S | 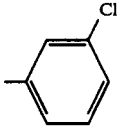 3-Cl-phenyl | 130 |
| 21 | $CH_3$ | $CH_3$ | CH | $SO_2$ | 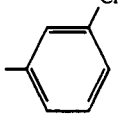 3-Cl-phenyl | 191–193 |
| 22 | $CH_3$ | $CH_3$ | CH | S | 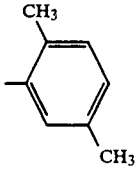 2,4-di-$CH_3$-phenyl | 122–123 |
| 23 | $CH_3$ | $CH_3$ | CH | $SO_2$ | 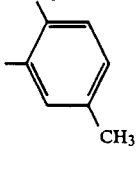 2,4-di-$CH_3$-phenyl | 136–138 |
| 24 | $CH_3$ | $CH_3$ | CH | S | 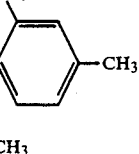 2,5-di-$CH_3$-phenyl | 104–106 |
| 25 | $CH_3$ | $CH_3$ | CH | $SO_2$ | 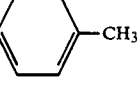 2,5-di-$CH_3$-phenyl | 158–162 |

TABLE 2-continued

| Example No. | R¹ | R² | A | X | Ar | Melting point/°C. |
|---|---|---|---|---|---|---|
| 26 | $CH_3$ | $CH_3$ | CH | S | 2-pyridyl | 137 |
| 27 | $CH_3$ | $CH_3$ | C—Cl | S | 2-chlorophenyl | |
| 28 | $CH_3$ | $CH_3$ | C—Cl | $SO_2$ | 2-methylphenyl | |
| 29 | $CH_3$ | $CH_3$ | C—Cl | S | 2,4-dimethylphenyl | |
| 30 | $CH_3$ | $CH_3$ | C—Cl | S | 2-methylphenyl | |
| 31 | $CH_3$ | $CH_3$ | C—Cl | $SO_2$ | 2,4-dimethylphenyl | |
| 32 | $CH_3$ | $CH_3$ | C—Cl | $SO_2$ | 2-chlorophenyl | |

Use Example

In the following Use Example, the compound listed below is employed as comparison substance:

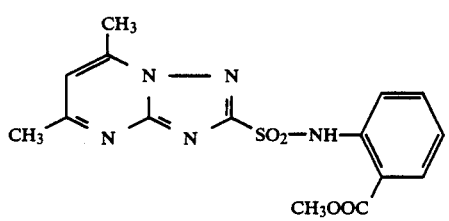

(A)

Example A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in damage in comparison to the development of the untreated control. The figures denote:
0% = no action (like untreated control)
100% = total destruction In this test, for example the compounds of Preparation Examples 24 and 25 show a clearly superior herbicidal activity against dicotyledon weeds compared with the comparison compound (A), while having a similar selectivity towards crop plants.

It is understood that the specification and examples are illustrative but not limitative of the present invention and that other embodiments within the spirit and scope of the invention will suggest themselves to those skilled in the art.

We claim:

1. A triazolo pyrimidine or the formula

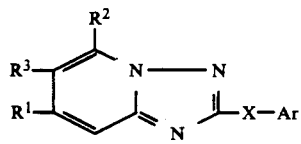

where $R^1$ and $R^2$ are hydrogen or lower alkyl, $R_3$ is hydrogen, X is —S— or —S(O)$_2$—, Ar is phenyl which is unsubstituted or mono to tri substituted by identical or different substituents selected from the group consisting of methyl, ethyl, tertiary butyl, fluorine, chlorine and methoxy.

2. A compound according to claim 1, wherein such compound is 2-(2,4-dimethylphenylthio)-5,7-dimethyl-1,2,4-triazolo[-1,5-a] pyrimidine of the formula

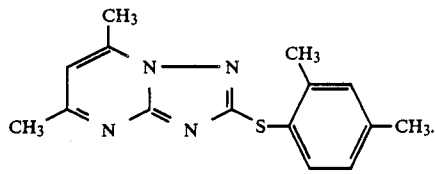

3. A compound according to claim 1, wherein such compound is 2-(2,4-dimethylphenylsulphonyl)-5,7-dimethyl-1,2,4-triazolo[-1,5-a] pyrimidine of the formula

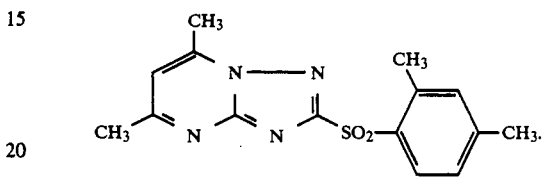

4. A herbicidal composition comprising a herbicidally effective amount of a compound according to claim 1 and a diluent.

5. A method of combating unwanted vegetation which comprises applying to such vegetation or to a locus from which it is desired to exclude such vegetation a herbicidally effective amount of a compound according to claim 1.

6. The method according to claim 1, wherein such compound is 2-(2,4-dimethylphenylthio)-5,7-dimethyl-1,2,4-triazolo[-1,5-a] pyrimidine.

7. The method according to claim 5, wherein such compound is 2-(2,4-dimethylphenylsulphonyl)-5,7-dimethyl-1,2,4-triazolo[1,5-a]-pyrimidine.

* * * * *